United States Patent [19]

Bernstein et al.

[11] Patent Number: 4,863,611
[45] Date of Patent: Sep. 5, 1989

[54] EXTRACORPOREAL REACTORS CONTAINING IMMOBILIZED SPECIES

[75] Inventors: Howard Bernstein, Cambridge, Mass.; Margaret A. Wheatley, Media, Pa.; Robert S. Langer, Somerville, Mass.

[73] Assignee: Massachusetts Institute of Technology, Cambridge, Mass.

[21] Appl. No.: 44,245

[22] Filed: Apr. 30, 1987

[51] Int. Cl.[4] .............................................. B01D 15/02
[52] U.S. Cl. ................................... 210/661; 210/196; 210/280; 210/289; 210/291; 210/502.1; 210/679; 210/805; 210/807
[58] Field of Search ............... 210/661, 679, 805, 807, 210/194, 196, 270, 275, 279, 280, 289, 291, 293, 507.1; 435/2, 174, 195, 177, 178, 179, 180, 288; 502/401, 402, 404

[56] References Cited

U.S. PATENT DOCUMENTS

| | | | |
|---|---|---|---|
| 4,243,532 | 1/1981 | Tsuda et al. | 210/196 |
| 4,266,029 | 5/1981 | Branner-Jorgensen | 435/177 |
| 4,373,023 | 2/1983 | Langer et al. | 435/2 |
| 4,412,923 | 11/1983 | Capitani et al. | 210/661 |
| 4,490,290 | 12/1984 | Gani et al. | 210/679 X |
| 4,666,425 | 5/1987 | Fleming | 435/177 |

FOREIGN PATENT DOCUMENTS

3406562A1  8/1985  Fed. Rep. of Germany .

OTHER PUBLICATIONS

Porath et al., *J. Chromat.*, 60, 167 (1971).
Axen et al., *Eur. J. Biochem.*, 18, 351 (1971).
March et al., *Anal. Biochem.*, 60, 149 (1974).
Kohn et al., *App. Biochem. and Biotech.*, 9, 285 (1985).
Hearn et al., *J. Chromat.*, 185, 463 (1979).
Chapman et al., *Clinica Chimica Acta.*, 118, 129 (1982).
Bethel et al., *J. Chromat.*, 219, 353 (1981).
Bethel et al., *J. Chromat.*, 219, 361 (1981).
Sanderson et al., *Immunology*, 20, 1061 (1961).
Turkova et al., *Collection Czech. Chem. Commun.*, 44, 3411 (1979).
Linker et al., *Bioch.*, 11, 563 (1972).
Yin et al., *J. Lab. Clin. Med.*, 81, 298 (1973).
Estes, *Curr. Therapeut. Res.*, 18, 58 (1975).
Lam, *Biochem. Biophys. Res. Commun.*, 69, 570 (1976).
Jacques, *Pharmacol. Rev.*, 31, 99 (1980).
Ph.D. Thesis of Howard Bernstein, M.I.T. 8/23/85.
Langer et al., *Science*, 217:261 (Jul. 16, 1982).

Primary Examiner—W. Gary Jones
Attorney, Agent, or Firm—Hamilton, Brook Smith & Reynolds

[57] ABSTRACT

An apparatus for removing material from a biological solution consisting of a reactor chamber having an inlet and an outlet, a bioactive compound immobilized on particular supports within the reactor, means for retaining the particular supports within the reactor, means for recirculating the solution and the supports at a high flow rate within the reactor, and means for agitating or dispersing the recirculating solution-support mixture throughout the reactor chamber so as to prevent packing of the supports while not subjecting the solution to excessive or damaging forces.

In the given example, an apparatus for the extracorporeal removal of heparin from blood is provided. Heparinase is immobilized on cross-linked agarose beads recirculated at a high flow rate through the reactor. Agitation of the blood-bead mixture sufficient to prevent packing of the beads within the reactor chamber is provided by means of a series of openings in the recirculation tube dispersing the mixture throughout the chamber.

15 Claims, 1 Drawing Sheet

EXTRACORPOREAL REACTORS CONTAINING IMMOBILIZED SPECIES

BACKGROUND OF THE INVENTION

The United States government has rights to this invention by virtue of National Institute of Health Grant No. NIH-5-RO1-25810-08.

This invention is generally in the area of methods and devices for neutralizing chemical species in vivo, and is a method and extracorporeal reactor utilizing high surface area substrates.

Extracorporeal systems perfused with whole blood have been an effective component in the treatment of kidney, heart and lung dysfunction for many years. Unfortunately, the artificial surfaces of machines such as dialysis units and oxygenerators potentiate thrombi and emboli formation. Physicians must therefore rely on systemic heparinization to provide blood compatibility.

Unfortunately, heparin, a mucopolysaccharide consisting of alternating D-glucosamine and D-glucuronic acid subunits and having a molecular weight between approximately 6,000 and 20,000, leads to hemorrhagic complications in many patients. Despite efforts to improve anticoagulation techniques, many patients develop disabling complications when these devices are used in conjunction with heparin. Of the approximately 20,000,000 extracorporeal procedures performed yearly, from 8 to 33% of the patients develop coagulation abnormalities, some of which are life threatening. With increased use of the relatively new membrane oxygenators one can expect longer continuous perfusion times and, in conjunction, the aggravation of these heparin induced problems. Efforts to inject the heparin locally or to otherwise immobilize or remove the heparin have either not been successful in preventing blood clots or have been unable to work in conjunction with high blood flow rates.

Incorporation of a blood filter capable of removing or neutralizing heparin would enable anticoagulation of the extracorporeal circuit while limiting systemic exposure to heparin. The availability of this type of device might allow the use of artificial organs or filters in patients who previously would have been subject to too great of a risk.

U.S. Pat. No. 4,373,023 to Robert S. Langer et al teaches using immobilized heparinase to degrade and neutralize heparin in blood. The examples demonstrate that the heparinase can be effectively bound to agarose beads and reacted with the heparin. Unfortunately, when this embodiment was tried on blood at clinical flow rates, the agarose beads packed or disintegrated and the device became unusable. The device described was also useful only in series with other blood treatment devices, not being incorporable into pre-existing devices used for blood treatment.

Another such device, taught by German Offenlegungsschrift DE 3406562 A1 to Fraunhofer-Gesellschaft zur Forderung der angewandten Forschung, has heparin degrading enzymes chemically bound to one side of a membrane having a pore size allowing molecules of less than 25,000 to 30,000 molecular weight to pass through. The apparatus is designed to inactivate that heparin in the bloodstream which is able to pass through the membrane. However, this device is unable to provide the high rates of heparin conversion desired clinically due to the requirement that the heparin diffuse through a porous membrane before contacting the enzyme. This limitation is particularly severe considering the high flow rates and thus the short residence time of the heparin in the devices. There are many other similar devices that have been tried with a variety of enzymes and reactive species. Unfortunately, these were also unable to deal with flow rates typical of clinical extracorporeal devices, especially in conjunction with biological solutions containing fragile cells and easily activated processes, such as the complement and coagulation systems in blood.

There are many situations requiring removal of toxins or other chemical species from the blood, in addition to heparinization. There are also a number of industrial or research processes, as in some fermentation processes, where on-line removal is desirable but not achievable due to the nature of the required flow rates in combination with the fragile character and high density of the cells.

It is therefore an object of the present invention to provide a method and device for continuous removal of chemical species from biological solutions at relatively high flow rates.

It is a further object of the present invention to provide such a method and devices utilizing bioactive compounds immobilized on a support material which is hemocompatible, mechanically stable, and has structural integrity.

It is a still further object of the present invention to provide a multipurpose device for treatment of labile or fragile biological solutions including whole blood.

SUMMARY OF THE INVENTION

A reactor containing immobilized species on a substrate having a very high surface area which is capable of treating biological solutions, especially blood, at high flow rates without damaging the biological materials. The reactor can contain immobilized species such as enzymes, antibodies, receptors, drug binding molecules or cofactors and thus can be made highly specific for the compound of interest. Alternatively, or in addition, non-specific solid phase adsorbents can be used to remove chemical species.

The reactor consists of a chamber with an inlet and an outlet which is fitted with a mesh at the outlet of the device for restraining porous particular supports within the chamber. These provide a high internal surface area, up to several orders of magnitude higher than the equivalent volume of hollow fibers or planar sheets, for the binding of large quantities of protein with the potential for high capacity removal.

Up until the present invention, the use of particular particles for extracorporeal reactors has been limited by the packing of the solid phase in the device. In order to use an extracorporeal reactor with particles at clinically useful blood flowrates, ranging from 100–1000 ml/min, a method of maintaining the beads in a fluidized state is required. In the present invention, the particular supports are maintained in suspension in the reactor by a combination of high speed recirculation and multidirectional agitation away from the direction of recirculation. The particles are formed of a biocompatible material such as crosslinked agarose which is selected for stability both to the biological solution and to the agitation. The particles are limited to a size range between that which can be freely recirculated and agitated by the reactor and that which can be restrained within the reactor. The maximum flow rate is limited by the stability of the particles. 8% crosslinked agarose particles can withstand flow rates up to 250 ml/min. Structurally stronger materials are required for high flow rates.

The reactor must meet specific stringent guidelines for clinical use. The first consideration is biocompatibility of the entire system. The device must not cause hemolysis, platelet aggregation, leukocytopenia, antibody formation, nor release toxic byproducts. The removal system must be compatible with clinical blood flow rates and have an operable life greater than the required perfusion time. At the same time, for some applications, the filter volume must be minimized to allow priming of the circuit with the patient's own blood supply. Finally, the system must be easily operable by the hospital personnel.

In the following example of a device meeting clinical requirements for blood flow rates and safety, spherical particles with diameters of 30–400 microns are used in a reactor having a mesh cutoff size of 25 microns. The chamber volume is at least 100 ml but not greater than 1 liter and includes a long U tube, formed of an inert material such as silastic having an inner diameter of 6–10 mm and an approximate length of 24 inches. The silastic line is fitted with six pairs of holes 2.5 mm in diameter and is attached to a peristaltic pump. When crosslinked agarose particles are used, the peristaltic pump is set to recirculate the reactor contents at a flowrate of at least 1200 ml/min but not greater than 1800 ml/min. This maintains a well mixed system and prevents the packing of the solid material. Flowrates through the reactor of greater than 100 ml/min are possible. In this example of a device for the removal of heparin from patients undergoing extracorporeal therapy, the reactor contains immobilized enzyme such as heparinase or other heparin degrading or neutralizing compound immobilized to the porous spherical support.

DETAILED DESCRIPTION OF THE INVENTION

Figure 1:
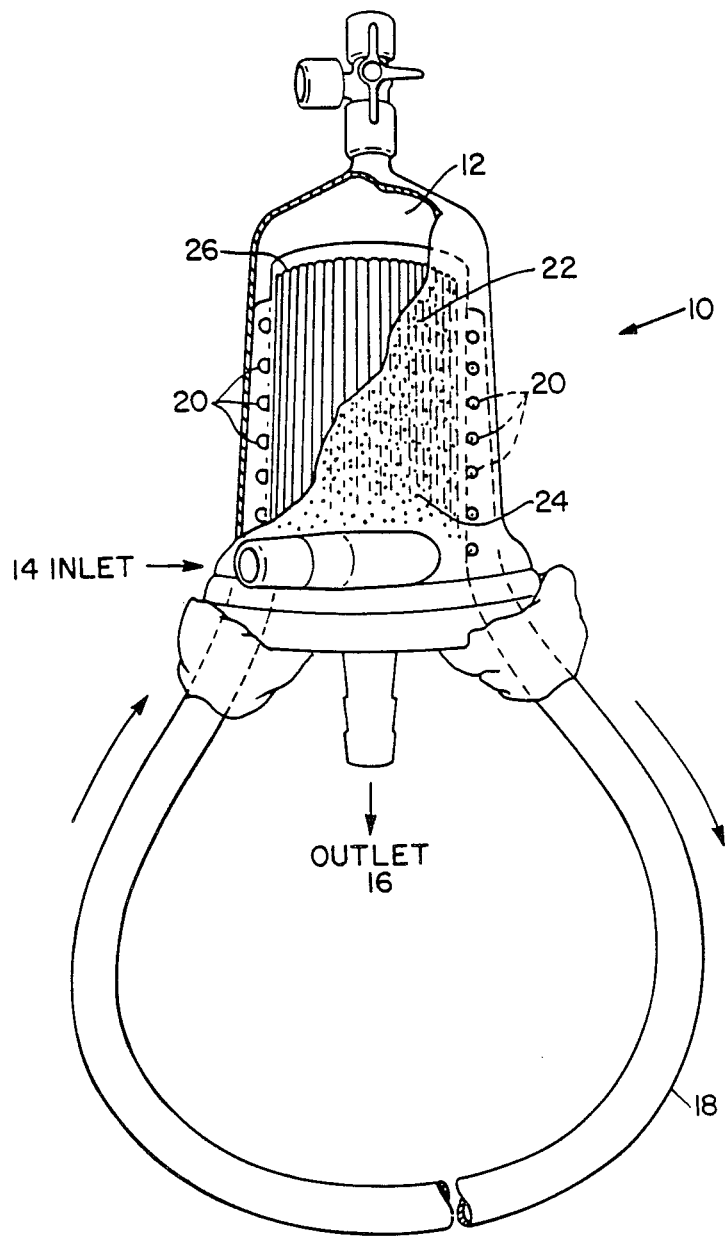
FIG. 1 is a plan view of a reactor according to the present invention, partially in section.

The method of the present invention is to construct a reactor containing a bioactive compound, such as heparinase, immobilized on a biocompatible support having sufficient surface area, binding capacity, and structural integrity to allow the reaction of the compound with clinical levels of substrate in a circuit containing a biological solution circulating at flow rates ranging from 10 ml/min up to one 1/min. A key element of the present invention is the inclusion of means for sufficiently agitating the incoming solution to maximize contact of the bioactive compound with the substrate, while preventing packing of the underlying support.

In the primary application of a device constructed according to this method, heparin is removed from blood in series with an extracorporeal device such as a dialysis unit or a blood oxygenator. Although the device is described in this context, it is easily modified by one skilled in the art of filtration of biological solutions for use in the removal of other substances or with other biological solutions such as cell culture fluids.

The device consists of a reactor chamber having an inlet and an outlet, a bioactive compound immobilized on porous particular supports within the reactor, means for retaining the supports within the reactor, means for recirculating and agitating or dispersing the recirculating solution-supports within the reactor chamber to prevent packing of the supports, wherein the agitation is limited to avoid subjecting the solution to excessive or damaging forces.

The support should meet the following requirements, as applied to a heparinase reactor:

The support material must covalently bind the heparinase to form an insoluble complex, the immobilized heparinase must retain adequate activity towards the substrate heparin, the immobilized enzyme must retain adequate thermal stability for use in a blood filter, the polymer support must be stable under the conditions of its planned use, i.e. it should not be chemically or enzymatically degraded by blood, the support and immobilized enzyme must be blood compatible, and the support should have good flow characteristics and low compressibility under clinical flow rates in the range of 150–250 ml/min through the reactor.

Suggested materials include agarose, cross linked dextran, polyhydroxyl ethyl methacrylate, polyacrylamide, cellulose, and derivatives or combinations thereof, preferably in the form of porous spheres. Cellulose acetate has previously been successfully used in extracorporeal devices. Cellulose contains hydroxyl functionalities which can be activated with tresyl chloride, cyanogen bromide, carbodiimidazole or periodination. This resin, structurally stable at 37°C., has mechanical characteristics which enable its use in filters even at high flow rates. Polyurethane is particularly blood compatible. Some of the current blood filters for clot removal use this material. Polyurethane immobilized heparinase has been prepared by reacting freeze dried purified heparinase with polyethylene glycol (PEG) capped toluene diisocyanate prepolymer.

The preferred material is agarose, a naturally occurring hydrophilic polymer. A beaded gel with a porosity of from 90–96% is formed by varying the percentage of agarose. The molecular weight of the gel ranges from 0.5 million for 10% agarose to 20 million for 4% agarose. Particle diameters ranging from 20 to 200 microns are commercially available.

Depending on the conditions within the reactor, it may be desirable to treat these materials to increase their structural strength. For example, in studies of heparinase bound by CNBr activation to 4% agarose beads, in vivo flow rates of 250 ml/min caused the agarose beads to fracture. The mechanical strength of agarose beads can be increased by either increasing the percentage of agarose or crosslinking the beads with epichlorohydrin or 2,3 dibromopropanol, using the method of J. Porath et al. in *J. Chromat* 60, 167 (1971). This allows a corresponding increase in the maximum operating pressure (a fifty percent increase in agarose leads to a two to four fold increase in the maximum operating pressure).

The particles are placed within the reactor chamber. The solution to be reacted with the bioactive compound is then circulated through the reactor chamber. Commercially available units for dialysis, blood exchange or oxygenation can be adapted for use as the reactor chamber.

The criteria to determine the appropriate coupling method are: minimization of leakage of the bioactive compound from the support, maintenance of the thermal stability of the compound, and retention of the optimum amount of bioactivity. The technique must also not cause a deterioration in the support material or the production of reactive groups on the support which would bind blood components in vivo. The enzyme must also retain its activity over time.

Bioactive compounds which are useful in the present invention include antibodies, enzymes, materials which non-specifically bind ions or chemical species, cofactors, drug binding molecules, etc. In the preferred embodiment for removal of heparin from the blood, the compound is an enzyme which degrades heparin or low molecular weight derivatives of heparin such as heparinase (EC-4.2.2.7), glucuronate-reductase (EC-1.1.1.19), O-sulfatase, N-sulfatase, beta-glucuronidase (EC-3.2.1.31), and aldose-reductase (EC-1.1.1.21). There are a number of other enzymes having utility in extracorporeal treatment including asparaginase and carboxypeptidase in the treatment of cancer, bilirubin oxidase for the treatment of jaundice, and possibly phenyalanine ammonia lyase in the treatment of phenylketonuria.

A preferred method for binding heparinase to agarose beads is by cyanogen bromide coupling, diagrammed as follows: (where L = ligand)

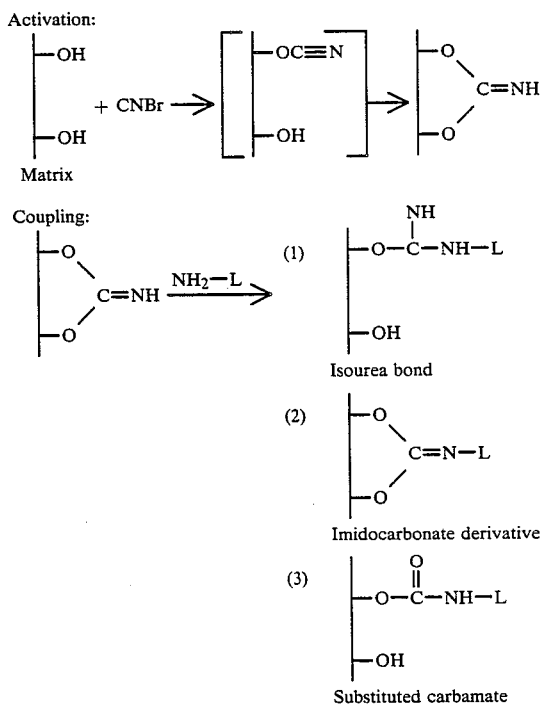

Two methods for activating free hydroxyl groups using cyanogen bromide as the activating reagent have been developed. The first, taught by Axen et al, *Eur.J-.Biochem.* 18, 351 (1971) and March et al, *Anal. Biochem.* 60, 149 (1974), employs cyanogen bromide directly as the activator in the presence of a strong base such as sodium hydroxide or sodium carbonate. A second, more efficient method in terms of overall yield of reactive groups is taught by Kohn et al., *Applied Biochem.and Biotech.* 9, 285 (1985). This method involves the use of an organic amine as a catalyst in conjunction with cyanogen bromide and is performed at non-alkaline pH.

Other methods producing a linkage between an enzyme and an insoluble polysaccharide support known to those skilled in the art include carbodiimidazole activation, described by M. T. W. Hearn et al., in *J. Chromat.* 185, 463 (1979); R. S. Chapman et al.,in *Clinica Chimica Acta.* 118, 129 (1982); G. S. Bethel et al., in *J. Chromat.* 219, 353 (1981); and G. S. Bethel et al., in *J. Chromat.* 219, 361 (1981), which forms urethane esters with no net charge at the polymer backbone. The urethane bond which is produced is reported to be quite stable. Still another method for immobilizing enzyme to a support is periodination, described by C. J. Sanderson et al., in *Immunoloqy*, 20, 1061 (1971) and J. Turkova al , in *Collection Czechoslova Chem. Commun.* 44, 3411 (1979) which uses aqueous solvents to form carbinolamines, yielding alkylamines upon reduction of the support. The conditions for reaction are mild and have the advantage of using aqueous solvents.

Variations in the degree of activation of the support influences the amount of enzyme bound as well as the retention of enzymatic activity. Binding of multiple amino groups within the active site to the support can decrease the activity of the enzyme. The strength of the bond between the enzyme and the support also limits the maximum allowable flow rate due to the increased likelihood of enzyme shearing from the carrier matrix. Crosslinking of the enzyme is sometimes effective in decreasing leakage. Unfortunately, 10% crosslinked agarose does not show any ability to degrade heparin in vivo.

To determine the chemical strength of the bond between the support and the enzyme, it is necessary to measure minute concentrations of proteins in buffer and in whole blood. Radiolabeling with $I^{125}$ which binds to the ring structure of tyrosine amino acids is used to label all proteins immobilized to the supports. Following dilution of the labelled sample with unlabeled heparinase, the enzyme is bound to supports via the appropriate coupling method. The coupled enzyme is then placed in a buffer solution and mildly agitated. Supernatants are checked for radioactivity as a function of time and temperature of incubation. In this way, the relative strength of the heparinase-support linkage undergoing mild agitation can be determined. Whole blood studies are used to examine the shearing effects on bound heparinase in various reactor geometries at physiological flow conditions.

A further factor which must be considered in optimizing the coupling method is the extent of distribution of the enzyme within the particles. The enzyme distribution during the cyanogen bromide immobilization procedure is dependent on the ratio of the rate at which the enzyme binds to the cyanate esters to the rate at which the enzyme diffuses within the pores of the particular support. The rate at which the coupling reaction occurs can be controlled by the amount of cyanogen bromide, pH, temperature, the speed at which the reaction mixture is stirred, and the size and charge of the enzyme being bound and the diameter and pore size of the particular support.

A model system can be developed to the required amount of enzyme and support, and the method for coupling of the enzyme to the support for removal of substrate from the blood. A number of factors must be taken into consideration, including specific and total enzyme activity after binding, stability of enzyme activity in vivo over time, and extent of reaction in vivo. For example, loss of heparinase activity occurs during prolonged exposure of the enzyme to body conditions of 37° C., pH 7.4 and biological agents. The process of inactivation is usually irreversible and results from conformational changes induced by heat, pH and chemical agents. Heating accelerates the process of enzyme unfolding, pH alters the charges of the various ionizable groups present in the enzyme and chemical agents irreversibly bind to the enzyme or degrade it. Since the loss of enzymatic activity must be considered in the loading of enzyme into the system, the loss of thermal stability during the immobilization step is a constraint in choosing the optimal coupling method. For example, for optimal retention of activity during coupling of heparinase, the pH must be kept at a pH greater than approximately pH 8.

The half-lives of the immobilized enzyme in buffer and in whole blood are measured by incubating a sample at the temperature of interest (for example, 37° C.) in the appropriate medium. The activity of the support as it degrades the substrate is measured as a function of time. In buffer, the assay for heparin is an ultraviolet assay described by A. Linker and P. Hovingh in *Bioch.* 11, 563 (1972). In whole blood, clotting assays are used: factor Xa, APTT, thrombin-antithrombin III, as descried by E. T. Yin et al., in *J. Lab. Clin. Med.* 81, 298 (1973); J. W. Estes in *Current Therapeut. Res.* 18, 58 (1975); L. H. Lam in *Biochem. Biophys. Res. Commun.* 69, 570 (1976); and L. B. Jacques in *Pharmacol. Reviews,* 31, 99 (1980). The optimal immobilization technique ideally should not decrease the thermal stability of bound heparinase at 37°C.

The biocompatibility, the mechanical strength, and the structural integrity of the material must be reevaluated after binding of the enzyme before use in vivo. To study biocompatibility, treated and untreated materials should first be checked in vitro for any hemolysis, leukocytopenia, platelet aggregation and any thrombosis. Immobilized enzyme and support material alone should produce equivalent changes in the levels of formed blood components (red blood cells, white blood cells and platelets) which exit the material. Mechanical strength and structural integrity are then tested. Hemocompatibility and consistent maximum flow rates at given pressures must be maintained.

The system must then be tested in circuit with an extracorporeal device. The in vitro studies follow substrate conversion as a function of flow rate, reactor volume, inlet substrate concentration and enzyme concentration. Hemocompatibility testing is performed concurrently. This includes inlet and outlet evaluation of the formed blood components and their relation to the reactor performance. These performance studies are not expected to mimic exactly the reservoir blood system used in the in vivo cases. The blood viscosity, formed blood components and coagulability characteristics will govern the fluid dynamics and mass transfer in the system and, thus, the overall reactor performance.

The supports must be maintained in a fluidized state in order to prevent packing of the spherical supports. This is accomplished during recirculation of the fluid by agitation of the particles. Agarose is compressible and it is difficult to achieve flowrates greater than 40 ml/min using a packed bed configuration. A number of methods have been tried without success. Experimentally, the extent of mixing can be shown using a labelled tracer, either radiolabelled or a dye such as blue dextran with a molecular weight of 2 million which does not physically absorb to the agarose particles. The modelling parameters are taught by Howard Bernstein in "A System for Heparin Removal", pH.D. Thesis, Massachusetts Institute of Technology, catalogued May 1986, the teachings of which are hereby incorporated by reference.

The following non-limiting example of a modified continuous flow reactor demonstrates the successful reduction to practice of a reactor including heparinase bound spherical supports which are retained within the reactor by a mesh without packing due to intra-reactor agitation of the recirculating fluid.

The reactor 10 shown in FIG. 1 consists of a reactor chamber 12 (a modified Bentley AF-10 arterial filter fitted with an internal recirculation line), an inlet 14, an outlet 16, a silastic tubing 18 having multiple holes 20, a bed 22 of porous spherical particles 24 with bound heparinase, and a porous mesh 26 for retaining the spherical particles 24. The Bentley Laboratories AF-10 blood filter is provided with a polycarbonate housing and a 25 micron pleated nylon mesh. The internal volume of the reactor is 250 ml. A packed bead volume of 85–100 ml was used. 8% agarose particles (Biogel A1.5, Biorad Laboratories, Rockway, N.Y.) crosslinked with 2,3 dibromopropanol were selected as having the highest retention due to structural stability in the reactor, as well as the highest percentage of retained activity, as shown by Tables 1 and 2.

TABLE 1

Effect of Agarose Content on Heparinase Immobilization

| % Agarose | % Activity Recovered |
|---|---|
| 4 | 45 ± 8 (N = 15) |
| 6 | 40 ± 7 (N = 2) |
| 8 | 40 ± 8 (N = 10) |
| 10 | 43 ± 7 (N = 8) |

TABLE 2

In vivo Percent Recovery of Beads Primed to the AF-10 Reactor of FIG. 1 (flow rate = 200 ml/min)

| % Agarose | % Beads Recovered |
|---|---|
| 4 | 50 ± 4 (N = 4) |
| 6 | 90 ± 6 (N = 3) |
| 8 | 98 ± 4.6 (N = 8) |
| 10 | 98 ± 3 (N = 6) |

Although this reactor utilized an elastic tube with six holes (sized large enough to allow the support particles to freely pass through) to thoroughly mix and disperse the support-solution mixture, other mechanical means could be used to achieve the same goal. By way of example, other mechanical means would include a Venturi pump or an array of tubes emptying into the reactor chamber, rather than one tube with multiple openings through which the support-solution mixture is dispersed within the reactor. The means for recirculation can be the same as the means for agitation, as in this example where both recirculation and agitation is achieved through manipulation of an elastic tube, or two separate devices can be utilized. As discussed above, the system can be optimized empirically, monitoring mixing by the addition of a colored dye or a radiolabelled tracer. The agitation must be limited to not activate the complement or coagulation systems while being sufficient to prevent packing of the support in "dead" areas. The effect of the recirculation rate on the extent of agitation required should also be determined and the two forces optimized for the particular solution to be treated.

The reactor was tested in three sheep at a whole blood flow rate of 110 ml/min. Recirculation rates of between 570 and 1800 ml/min were used. Effective removal without problems for the sheep was obtained with this device only when the recirculation rate was between 1200 ml/min and 1800 ml/min. The reactor removed 20-60% of the heparin in a single pass through the device. The extent of conversion was determined primarily by the volume of agarose, the immobilized heparinase activity, the inlet heparin concentration, and the plasma antithrombin level. The reactor unit without immobilized enzyme can be sterilized with ethylene oxide for use with human patients. The immobilized enzyme can be sterilized by gamma irradiation.

The present invention of immobilizing a bioactive compound such as heparinase in a device having high surface area, biocompatibility, and mechanical strength for extracorporeal treatment of blood or other biological solutions has been described with reference to specific embodiments. Other variations and modifications will be obvious to those skilled in the art from the foregoing detailed description of the invention. Such variations and modifications are intended to come within the scope of the appended claims.

We claim:

1. An apparatus for removing material from a biological solution by passing the solution through a reactor and contacting the solution with a bioactive compound, the apparatus comprising:
   a reaction vessel which defines a reactor chamber having an inlet and an outlet;
   particulate supports for said bioactive compound, said particulate supports capable of being fluidized as said solution is passed through the reaction vessel;
   means for retaining said fluidized particulate supports within said reactor chamber;
   a bioactive compound immobilized on the particulate supports, wherein said compound will interact with the material to be removed from the biological solution;
   means for recirculating the biological solution within said reactor chamber comprising a tubular member and a pump and wherein the ends of said tubular member are within said reactor chamber; and
   means for providing multi directional agitation to the biological solution and particulate supports to maintain the particulate supports in a fluidized state when the flow rate of said biological solution entering said reactor is between approximately 10 ml/min and 1000 ml/min said means for providing a multi-directional agitation comprising a multiplicity of holes in said tubular member inside of said reactor chamber, said holes dispersing said recirculating solution throughout said reactor chamber.

2. The apparatus of claim 1 wherein said bioactive compound is selected from the group consisting of enzymes, antibodies, cofactors, receptors, drug binding molecules or combinations thereof.

3. The apparatus of claim 2 wherein said solution is heparinized blood and said bioactive compound is heparinase.

4. The apparatus of claim 1 wherein said supports are selected from the group consisting of ion-exchange resins, agarose, cellulose, cross linked dextran, polyhydroxyl ethyl methacrylate, polyacrylamide, polyurethane, and derivatives or combinations thereof.

5. The apparatus of claim 4 wherein said supports are crosslinked agarose beads.

6. The apparatus of claim 1 wherein said supports have particle diameters ranging from 20 to 200 microns.

7. The apparatus of claim 1 wherein said retaining means is a mesh having a pore size smaller than the diameter of said supports.

8. The apparatus of claim 1 wherein said pump is capable of recirculating said solution and supports within said reactor chamber at a flow of between approximately 1200 ml/min and 1800 ml/min.

9. A method for removing material from a biological solution by passing the solution through a reactor containing a bioactive compound, said method comprising:
   providing an apparatus having a reaction vessel which defines a reactor chamber having an inlet and an outlet; particulate supports for said bioactive compound, said particulate supports capable of being fluidized as the solution is passed through the reaction vessel; means for retaining said particulate supports within said reactor chamber; a bioactive compound immobilized on the particulate supports, wherein said compound will interact with the material to be removed from the biological solution; means for recirculating the biological solution within said reactor chamber comprising a tubular member and a pump and wherein the ends of said tubular member are within said reactor chamber; and means for providing multi-directional agitation to the particulate supports to maintain said particulate supports in a fluidized state when the flow rate of said biological solution entering said reactor is between approximately 10 ml/min and 1000 ml/min said means for providing multi-directional agitation comprising a multiplicity of holes in said tubular member within said reactor chamber, said holes dispersing said recirculating solution throughout said reactor chamber; and
   flowing said biological solution through the apparatus while simultaneously providing recirculation and multi-directional agitation of the solution and the particulate supports contained within the reactor chamber.

10. The method of claim 9 further comprising selecting said bioactive compound from the group consisting of enzymes, antibodies, cofactors, receptors, drug binding molecules or combinations thereof.

11. The method of claim 10 further comprising selecting heparinase as said bioactive compound, wherein said biological solution is heparinized blood.

12. The method of claim 11 further comprising pumping the blood through said reactor at a flow rate of between approximately 10 ml/min and 1000 ml/min and recirculating the blood in said reactor chamber at a flow rate of between approximately 1200 ml/min and 1800 ml/min.

13. The method of claim 9 further comprising selecting said supports from the group consisting of ion-exchange resins, agrose, cellulose, cross linked dextran, polyhydroxyl ethyl methacrylate, polyacrylamide, polyurethane, and derivatives or combinations thereof.

14. The method of claim 13 wherein crosslinked agarose beads having diameters in the range of between approximately 20 and 200 microns are selected as said particulate supports.

15. The method of claim 9 further comprising providing a mesh having a pore size smaller than the diameter of said particulate supports as said retaining means.

* * * * *